United States Patent [19]

Timar

[11] 4,254,103
[45] Mar. 3, 1981

[54] HEPATOPROTECTOR FACTOR (HF) AND METHOD OF TREATMENT

[75] Inventor: Magdalena Timar, Bucharest, Romania

[73] Assignee: Institul de Cercetari Chimicofarmaceutice, Bucharest, Romania

[21] Appl. No.: 46,605

[22] Filed: Jun. 8, 1979

Related U.S. Application Data

[63] Continuation-in-part of Ser. No. 876,415, Feb. 9, 1978, abandoned.

[51] Int. Cl.³ .................. A61K 35/407; A61K 37/00; C07G 17/00
[52] U.S. Cl. ................................ 424/106; 260/236.5; 424/177
[58] Field of Search .............................. 424/106, 177; 260/236.5

[56] References Cited

U.S. PATENT DOCUMENTS

| | | | |
|---|---|---|---|
| 2,573,702 | 11/1951 | Folkers et al. | 424/106 |
| 2,658,020 | 11/1953 | Schoch | 424/106 |
| 3,034,963 | 5/1962 | Wachtel | 424/106 |

OTHER PUBLICATIONS

Booklet Retropofar.
Brochure, "A New Trend in Liner Therapy Tropofar". 11nd Round Table Conference, 4–5, Oct. 1977, re: Tropofar Factor Hepatoprotector–FH–Clinical Efficiency.
M. Timar, Chem. Abstr. 87, (1977) 49794x.
M. Timar, Chem. Abstr. 91, (1979) 186822b.

*Primary Examiner*—Delbert R. Phillips
*Attorney, Agent, or Firm*—Karl F. Ross

[57] ABSTRACT

A method of extracting a new liver-protecting pharmaceutical from the liver of cattle is disclosed as well as new pharmaceutical compositions and a method of treating cirrhosis of the liver or viral hepatitis.

2 Claims, 2 Drawing Figures

HEPATOPROTECTOR FACTOR (HF) AND METHOD OF TREATMENT

CROSS REFERENCE TO RELATED APPLICATION

This application is a continuation-in-part of Ser. No. 876,415 filed Feb. 9, 1978, now abandoned.

FIELD OF THE INVENTION

This invention relates to a method of extracting a new pharmaceutical useful in the treatment of liver cirrhosis and viral hepatitis. The invention relates further to new pharmaceutical compositions and to methods of treating liver cirrhosis and viral hepatitis.

BACKGROUND OF THE INVENTION

Little progress has been achieved in the past 30 years in the treatment of liver diseases as compared with treatment of diseases in other therapeutic fields. The reasons for this lagging are to be looked for both in the polymorphous character of liver diseases and in some principles applied so far in therapeutics.

The problem of liver therapeutics is a concern of long standing with clinicians, who have suggested the use of liver extracts as far back as the beginning of the twentieth century. See Gilbert, A. and Carnot, P., *Note preliminaire sur l'opotherapie hepatique*, Compt. rend. Soc. Biol., Aca. Sci. Paris, 48, 937 (1896). This therapy was practiced in the first half of this century. See Buettner, H. E., *Experimentelle und klinische Untersuchungen uber die Wirkung einspritzbarer Leberextrakte*, Fortschr. Therap., 11, 257–346 (Berlin 1935). Liver extracts or hydrolysates were prepared industrially, but they were not biologically standardized as to their liver-protecting effect. In the end it was agreed to determine the vitamin $B_{12}$ contents in these preparations, and considering the biological role of the vitamin to take it as a measure of their activity.

The outstanding progress of biochemistry in the last decades has shown a better understanding of the essential metabolic links in liver cell functioning. Attempts were made as a result to introduce certain components of these metabolic processes in the treatment of liver diseases. Products suggested for therapeutic use include mixtures of amino acids, purine and pyrimidine compounds, phospholipids, orotic acid, vitamins and sugars. The preparations are marketed under various pharmaceutical trade names such as Hapesteril, Essentiale, Purinor, Hepatofalk, Aspatofort, among others. Clinical results obtained with these preparations are limited. They are active only in the steady stage of liver disease and ineffective in the evolutive stage. The restricted effect of these preparations is due to the fact that they do not take into consideration a basic element in liver disease, namely, that they are in the first place determined by primary cell membrane damage. See Popper, H., *The Problem of the Hepatitis*, Amer. J. Gastroenterology, 4, v. 55, 335–346 (New York, 1971) and Popper, H., *Membrane Alterations as Basis of Liver Injury*, Falk Symposium, 22 (Basel, 1976). The passage through cell membranes in metabolic processes requires an active membrane transport, sometimes by means of a "carrier" substance, as in the case of aspartic and glutamic acids. The presence of this carrier in the membrane implies the morpho-functional integrity of the membrane, but this integrity is deficient in the course of liver diseases. As a result, the components of the various metabolic processes occurring in the liver, administered in the form of pharmaceutical preparations, fail to be integrated in the metabolic processes of the hepatocyte for lack of a carrier in the structure of the membrane. This is the limiting factor for the clinical efficacy of glutamic and aspartic acids in evolutive liver diseases.

Immunological studies in the last decade have proved that the mesenchyma is also involved in the membrane damage process by a mechanism of self-aggression. This finding has determined the introduction of certain steroids and immunosuppressives in therapeutical practice. Among the first structures to be used for this purpose are the corticosteroids, which have proved their effectiveness in severe clinical forms of both acute viral hepatitis and chronic aggressive hepatitis. However, in the course of the long term clinical use of these structures it becomes obvious that this pharmacotherapy was far from rational. See Sherlock, S. H., *Chronic Hepatitis and its Therapy*, Lecture Xth European Congress of Gastroenterology (Budapest, 1976) and Cook, G. C. et al, *Controlled Prospective Trial of Corticosteroid Therapy in Active Chronic Hepatitis*, Quart. J. Med., 40, 150–166 (London, 1971). It is shown in these references that in acute viral hepatitis, steroid therapy is the starting point for the development of liver cirrhosis in the subsequent evolution of patients so treated. For lack of a more adequate therapy, in chronic, aggressive hepatitis, the treatment with steroids and immunosuppressives is still used.

Under the circumstances it appeared necessary to reconsider the fundamental principles of the pharmacotherapy to be applied in liver diseases. Hence experimental pharmacological studies were conducted to elucidate the liver-spleen interrelation in respect to metabolic loading with various drugs. Since drugs may be considered as "foreign bodies" for the metabolic processes of the reticulo-endothelial system (RES), it must be assumed that many of the processes concerning the metabolism and elimination of the drugs are connected with the RES structures located in the liver and spleen. It is a well-known fact that the acetylation of sulphonamides is supported to the extent of 80% by Kupffer cells, and that the acetylation of bacterial toxines is achieved in RES dependent cell structures, resulting in the emergence of sulphonamide side-effects. See Govier, W. C. *Role of Kupffer Cells in Acetylation*, J. Pharmac. Exp. Therapy, 150, 305–310, (New York, 1965) and Freedman, H. M. et al *Dissociation of Antitoxic and Immunogenic Activities of Endotoxine by Acetylation*, Ann. N.Y. Acad. Sci. 2, v. 133663–667 (New York, 1966). The competition of two metabolic acetylations of the same cellular level is the reason for the side-effects of sulphonamides. If sulphonamides are administered for therapeutic purposes unless the RES dependent acetylation is concentrated on the bacterial toxines, a part of this metabolic process will be located in the spleen. Timar, M. et al, *Studies on Acetylation of Sulphamethoxypyrimidine in Endotoxine Tolerant Mice*, Biochem. Pharmacol., 21, Pergamon Press, 42–422 (Oxford, 1972). This example demonstrates that the molecular biology of the liver is first of all connected with RES dependent cell structures, which are located in the liver and spleen. See Timar, M., *Liver-Spleen Relationship in the Study of Liver Protecting Drugs*, Advances in Experimental Medicine and Biology, 73 A, 455–457 (New York, 1976) and Timar, M., *The Extrapolation of Liver Functionality Data From the Animal to the Human* in the Treatment of the Acute Stage of Liver Damage with FH, II Farmaco, ed. prat. No. 9, 473–478.

As already mentioned, steroid treated patients suffering from acute viral hepatitis will in some cases develop cirrhosis in their future clinical condition. Studies performed for the explanation of this side-effect of steroid therapy have highlighted the fact that during the regenerative processes in the liver, a leucine-containing peptide structure is secreted in the spleen. See Timar, M., *Cortisone Damaging Effect in Experimental Mitochondrial Liver Injury*, X[th] European Congress of Allergy and Immunology, Proceedings, 360364 (Prague, 1977). The peptide is involved in the protein synthesis processes in the liver. Its secretion occurs by a positive feedback mechanism between the liver and the spleen. The secretion of this peptide is inhibited by steroid therapy as well as by heliotropine, an alkaloid which is involved in the aetio-pathogeny of liver cirrhosis in the endemic area of Central Asia.

These experimental findings provided the baseline for research aimed at developing a new drug for the treatment of liver diseases which should preserve the trophic functions of the spleen. A complex peptide structure was discovered as a result. It is a component of the cell membranes of liver and is known as the liver-protecting factor (HF).

OBJECTS OF THE INVENTION

It is an object of the present invention to provide a method of extracting a liver-protecting substance known as the Hepatoprotector Factor (HF), also known as (FH), from the liver of cattle.

It is a further object of the invention to provide pharmaceutical compositions containing the Hepatoprotector Factor (HF) for the treatment of liver cirrhosis and viral hepatitis.

It is yet a further object of the invention to provide a method of treating liver cirrhosis or viral hepatitis by administration of a pharmaceutical composition containing the Hepatoprotector Factor (HF) to an afflicted patient.

DESCRIPTION OF THE INVENTION

Figure 1:
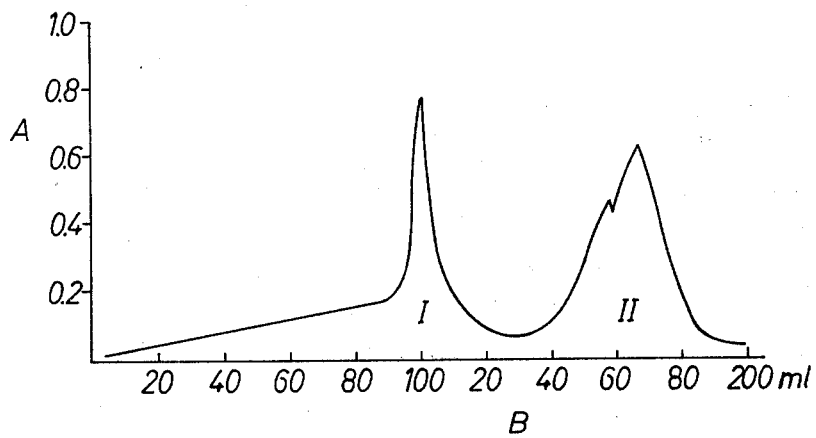
FIG. 1 is a graph of the relative absorbency A at 570 mm (ordinate) vs. ml of eluate (abscissa) showing the two ninhydrine-positive peaks of which the first I peak of the SP-Sephadex C-25 gel filtration represents the active fraction for the purposes of the invention.
Figure 3:
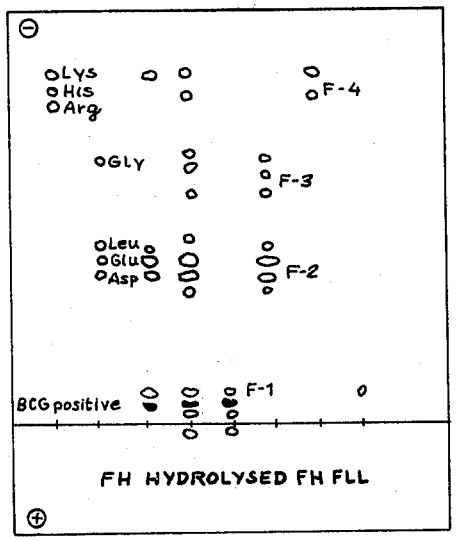
FIG. 3 represents a chromatogram thereof.

The new product for treatment of cirrhosis of the liver and viral hepatitis is obtained as an extract from the liver of cattle. The exact structure of the new product (Hepatoprotector Factor HF, also referred to as FH, i.e. Factor Hepatoprotector) has yet to be determined but it is known that it is a polypeptide containing the Asp and Glu moieties. See FIGS. 2 and 3. In any event the new product is obtained by the following procedure:

The cattle liver is minced and then treated with a solution of acetone in order to extract the Hepatoprotector Factor (HF) therefrom. The acetone extraction solution is preferably about a 70% solution and is preferably used in a ratio of 3 kg of acetone solution to 1 kg of minced cattle liver. The minced cattle liver is then pressed to separate the acetone solution containing the Hepatoprotector Factor (HF) from the minced cattle liver. The acetone solution containing the HF is then filtered to remove impurities. Next the acetone is evaporated to leave behind the Hepatoprotector Factor in the form of a liver extract. Fat is then extracted from the liver extract. Suitable extraction solvents include any hydrophobic organic solvent, for example benzine type A or carbon tetrachloride. The remaining liver extract is then subjected to gel filtration on a SP-Sephadex C-25 column. The liver extract is introduced to the column in the form of an aqueous solution and after the first absorption peak is found according to FIG. 1 is eluated with distilled water. The eluate obtained is then collected and subjected to lyophilization to effect concentration. The Hepatoprotector Factor is then recovered as a white powder.

The product obtained above may then be divided up. Each portion is then dissolved in distilled water. A solution is formed of about 60 mg product/ml of distilled water. The product may then be checked for quality by either elementary analysis, amino acid analysis, or high voltage electrophoresis and comparing the results against a known standard. The product is again subjected to lyophilization. The product is now ready to be formulated into suitable pharmaceutical compositions in admixture with a pharmaceutically acceptable carrier.

The method according to the invention for the treatment of liver cirrhosis or viral hepatitis consists in a daily administration i.m. or s.c. of 28 mg (one dose) of Hepatoprotector Factor (HF) for 30 days. As a consequence of this treatment the following therapeutical effects are characteristics 1. Improvement of subjective complaints of the patients, i.e. 4–5 days after the start of the treatment there occurs a progressive decrease of abdominal distension, bitter taste, nausea and the feeling of a burden in the right hypochondrium, with disappearance of drowsiness after meals, of asthenia and psychic depression.

2. Improvement of the objective symptoms, i.e. decrease of the hemorrhagic syndrome and the number of vascular stars and an increase in diuresis, even where previously other conventional therapies to gain such relief had failed. At the end of the treatment with Hepatoprotector Factor the ascites and oedema disappeared.

3. Improvement of the liver function, i.e.
   a decrease of the hepatocytolysis (ascertained by the transaminase values);
   an increase of conjugating function of liver cells (normalization of bilirubinaemia);
   an increase of protein synthesis (ascertained by increased amount of serum albumins and pseudocholinesterase activity);
   a decrease of mesenchymal inflammation (one month after the end of the treatment).

The duration of the Hepatoprotector Factor treatment—one-course efficacy—depends on the stage of the liver cirrhosis. The maximum therapeutic effect is noticed 1–2 months after the end of the treatment; in compensated liver cirrhosis another course should be repeated after 6 months, in decompensated cirrhosis after 3 months.

Figure 2:
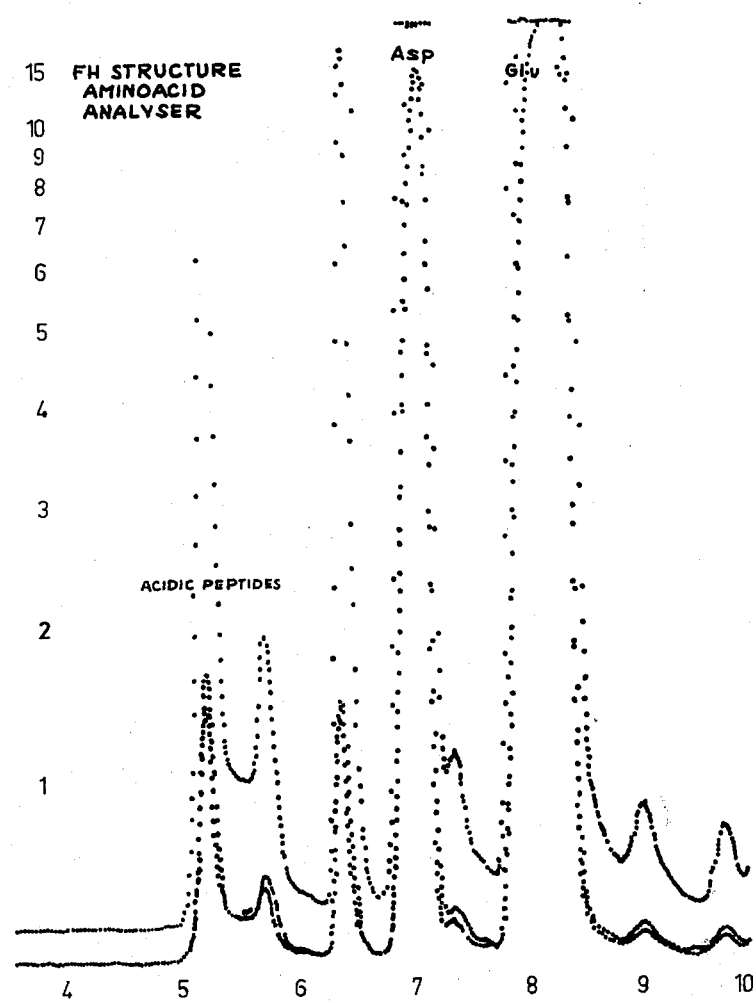
FIG. 2 is an amino acid analysis of the product of the invention.

4. The quality of the liver-derived Hepatoprotector Factor is ascertained chemically:
   by elementary analysis $C = 11.0 \pm 1.0$; $H = 2.3 \pm 0.5$; $N = 2.5 \pm 0.5$;

by amino acid analysis: glutamic acid=13.4%; aspartic acid=4.0% (see FIG. 2);

by high voltage electrophoresis on Whatmann 1 paper, 3000 V, 60 min., pH 1.9 formic acid (developed with 0.1% ninhydrine in acetone) 5 ninhydrine positive spots are noted located as follows: 1 between the start point and aspartic acid, 3 spots at the level of asp, glu, leu and 1 spot at the level of lys. For the migration, HF is used in a solution of 15 mg/ml distilled water, comparatively with molar solutions of asp, glu, leu, lys had to be spotulated 0.01 ml (see FIG. 3).

Biologically: The dose of 70 mg/kg male Wistar rats, Hepatoprotector Factor administered at 0, 6, 24 and 30 hours after intoxication of the animals with allyl alcohol (the method is described in the Journal "Il Farmaco, ed. prat. 1974, V. 29, page 243) causes a significant decrease in the amount of necrotic liver tissue and a decrease of hepatocytolysis ascertained by SGOT level in the blood serum.

The following is an example of how the HF extract is obtained.

EXAMPLE

The Hepatoprotector Factor (HF) represents a complex peptide structure and is obtained by the following method Fresh cattle liver is minced and subjected to extraction with acetone. For each kg of minced liver 3 kg of a 70% acetone solution is used for the extraction. The acetone and the minced liver are mixed for 4 hours. The liver tissue is separated from the acetone by pressing and the acetone solution containing the liver extract is filtered to eliminate impurities. Acetone is then separated from the liver extract by evaporation in a RAM apparatus. Next, fat is removed from the liver extract by treatment with benzine type A (gasoline). The extract obtained contains a ninhydrine positive substance. The extract is subjected to gel filtration on a SP-Sephadex C-25 column. A quantity of 200 ml of the above extract is introduced on a 100 cm Sephadex column and is eluated with 3 liters of distilled water. The obtained solution is collected and then concentrated by lyophilization yielding a white substance known as Hepatoprotector Factor (HF).

The HF is then divided up into portions. Each portion is placed in an individual vial and distilled water is added so that a solution of 60 mg HF/1 ml distilled water is obtained. The HF solution is then checked for quality using either elementary analysis, amino acid analysis or high voltage electrophoresis and comparing the results against a known standard. The solution is again subjected to lyophilization. The product may then be combined with pharmaceutically acceptable carriers to form pharmaceutical compositions.

The following tests show clinical results of treating patients with hepatitis and liver cirrhosis with the Hepatoprotector Factor (HF).

TEST 1

HF Efficacy in Ascitogen Liver Cirrhosis

Material and Methods 32 patients with ascitogenic cirrhosis were included in the clinical study. The lengths and strong character of the illness were different, such a variety contributing to the purpose of establishing the therapeutical limits of HF in different stages of cirrhosis evolution. Quarterly hospitalized, 3–4 times a year kept on a balanced salt-free diet, the patients were administered 3–4 courses (each course of 30 doses, one dose—28 mg/day/i.m.) of HF.

The evolution of subjective, objective symptoms and the liver functionality were determined before and during 2–3 years of HF treatment. The results obtained were evaluated separately, for the patients who died and for the survivors.

Results of Treated Patients

| Patient's Initials | age | sex | ascites b | ascites a | diuresis ml/day b | diuresis ml/day a | Bilirubinaemia (T) mg % b | Bilirubinaemia (T) mg % a | Albumin % b | Albumin % a | PChe U/m b | PChe U/m a |
|---|---|---|---|---|---|---|---|---|---|---|---|---|
| R.M. | 51 | M | + | − | 1000 | 1800 | 2.2 | 1.2 | 41 | 45 | 1.7 | 3.0 |
| R.A. | 73 | M | + | − | 900 | 1800 | 3.6 | 2.1 | 38 | 47 | 1.5 | 2.9 |
| L.I. | 52 | F | + | − | 1000 | 2200 | 0.8 | 0.6 | 42 | 51 | 3.9 | 6.0 |
| D.V. | 42 | M | + | − | 800 | 1700 | 0.6 | 0.5 | 34 | 44 | 1.9 | 4.5 | b = before treatment
a = after treatment

Results and Discussion

I. The HF influence on the subjective symptoms of PC appeared after a short time (4–5 days) after the beginning of the treatment and consisted in a fast improvement of the:

1. Dyspeptic syndrome (a progressive decrease of abdominal distension, of the feeling of a burden in the right hypochondrium, of inappetite, bitter taste, nausea).
2. Neuropsychic disturbances (the disappearance of drowsiness after meals, of asthenia and psychic depression).

II. HF influenced the objective symptoms, having an oscillating-wavy character: the symptoms improved or disappeared progressively, during the HF treatment and at the end of the treatment, but 3–4 months after the end of the HF treatment the symptoms reappeared and a new HF course influenced them again. Thus, the objective symptoms were influenced as follows:

1. The hemorrhagic syndrome (purpura, ecchymosis of the skin, gingival hemorrhages, expression of a deficiency in the clotting-factor synthesis) disappeared or decreased a short time after the beginning of the treatment, parallel with the improvement of the protrombine percentage (even where other therapeutic methods previously used had failed).
2. The vascular stars, expression of the hepatocyt to catabolize the oestrogen hormones and serotonine decreased in their number and intensity, in some patients till the disappearance during and after the end of the treatment.

3. The jaundiced color of the skin became normal parallel with the decrease of total bilirubine and the relationship between the direct and indirect bilirubine improved.
4. The hepatomegaly, when present, decreased a little in its volume and consistency due to the decrease in the mesenchymal inflammatory process, providing a possible explanation for the decrease of portal hypertension and feeling of a burden in the right hypochondrium.
5. The splenomegaly diminished in 50% of the patients parallel with the improvement of the hypersplenism phenomenon (especially the anemia and leucopenia).
6. The diuresis, which decreased in PC due to the aldosterone and ADH excess, insufficiently catabolized by the liver, increased during the treatment and remained at the level of 1200–1500 ml/day after the end of treatment.
7. The oedema and ascites decreased very impressively after the first HF course in the majority of the patients, even where other therapeutical methods previously used had failed.

The ascitogenic liver cirrhosis is characterized by the sclerotic process and liver cell regeneration which restrains the suprahepatic venus, inducing the portal hypertension; to these changes are added the hepatocyt-function disturbances characterized by a decrease of albumin synthesis, which is involved in an oncotic pressure decrease, and the aldosterone and ADH inactivation decrease determine the oliguria and ascitic-hydropigen syndrome.

In the appearance of ascites a basic role is represented in the increased hydrostatic pressure in the portal area. The oncotic pressure decrease is induced by the hypo- and dysproteinaemia, due to the absorption disturbances in the intestine and protein synthesis in the liver, and by protein loss after paracentesis and intestinal transudation. The lack of the relationship between the degree of portal hypertension and the intensity of ascites suggests the contribution to the ascites genesis of other factors. Roles are played by the colloidosmotic and hydrostatic pressure of the ascitic liquid and by the lymphatic circulation disturbances. The water extravasation induced by the hydrostatic and osmotic pressure disbalance provokes a decrease of volemia.

The disturbances of the water metabolism induce some kidney changes. The deficiency in the kidney perfusion is stimulated by the renin secretion angiotensin, aldosterone and ADH, which could not be inactivated by the cirrhotic liver cell, and water retention develops; the $Na^+$, $K^+$ depletion is followed by an increase of ascites and oedema.

HF decreased the mezenchymal inflammatory process in liver (the portal hypertension decrease), restored the hepatocyte functionality and by the inactivation of hormones in the liver the re-establishment of oncotic pressure occurs. By restoring the cell membrane permeability (filtration and kidney reabsorption) HF interrupts the genesis of ascitic-hydropigen syndrome.

8. The appetite, which is a sign of improvement in liver cirrhosis, increased and some of the patients increased their body weight; the diuresis increased and the oedema and ascites disappeared.

III. The HF efficacy on the liver functionality tests was characterized by the following:

1. Hepatocytolysis decrease (TGP, TGO—determined by the Reitman-Frankel method) noted after the treatment.
2. The restoring of the protein metabolism in the liver cell was proved by:
   (a) the proteinaemia (Abbed's refractometric method) and A/G relationship increased progressively during the treatment.
   (b) the McLagan test (photometric method) had an oscillatory character (a progressive decrease, statistically not significant).
   (c) the serum cholinesterase (butirilcholinesterase, Birzu method) increased after the HF treatment, proving the increased protein synthesis in some of the patients.
   (d) the protrombine percentage recovered its normal value in 80% of the patients.
3. The restoring of the conjugating function of the liver was characterized by:
   (a) the decrease of total bilirubinaemia (Jendrassik-Clegharu method) in the cases where jaundice was present.
   (b) an increase of conjugated bilirubine.
   (c) an increase of BSP conjugation, statistically significant.

IV. The dynamic study of the evolution of 32 portal cirrhotic patients with ascites and hydropigen syndrome, treated with HF ascertained an improvement in 22 (68.75%) patients, in the first stage of decompensation. In 10 patients (31.25%) more than 50 years old and more than 5 years severely decompensated, the improvement due to HF was manifested only during the treatment; after the treatment, at different periods of time, the patients died by infectious diseases or superior digestive hemorrhages. The HF treatment in these patients was performed in order to ascertain the therapeutic limits of the efficacy of this drug in the severe form of liver cell decompensation.

Conclusions

1. HF is efficacious for the treatment of portal decompensated cirrhosis. HF induces an improvement in clinical symptoms and laboratory test results, especially in recently decompensated cirrhosis, in the first stage of decompensation.
2. HF efficacy is due to its influence on the decrease of portal hypertension by reducing the mezenchymal inflammatory process, restoring the complex liver cell functionality (protein synthesis, hormone inactivation) and by restoring the cell membrane permeability.
3. The HF treatment consists in repeated courses (30 doses per course, one dose 28 mg/day/i.m.) to be repeated every 3–4 months in patients with proper hygienic-dietetic conditions.

TEST 2

HF Efficacy in Chronic Aggressive Hepatitis and Liver Cirrhosis

Material and Methods

The study was carried out on 14 patients, 7 afflicted with chronic aggressive hepatitis and 7 with liver cirrhosis-portal decompensation; the patients were treated for 60 days with HF. The subjects were selected from the hospitalized patients in the II medical clinic, at Jassy, during July–December 1976. The experimental group had in its scope 10 females and 4 males, the average age being 50. The following study was performed, as recommended by the Committee on Drugs: the presence of the symptoms associated with the astheno-dyspeptic syndrome, the oedema, ascites, hepato- and splenomegalia, the laboratory tests as to the serines, globulines, SGPT, protrombine time, total bilirubine, the dysproteinaemia (Gross, thymol), total cholesterol, the BSP epuration and possible haematological changes.

The clinical symptoms were checked daily during the hospitalization, the laboratory tests being performed at the beginning of the treatment, 30 and 60 days after the treatment.

In the first 10 days HF was administered in doses of 56 mg/day/i.m. (a vial with 2 doses) and was continued for 50 days, administering 1 vial at an interval of 2 days. According to the schema of treatment, each patient received 35 vials of HF over a period of 60 days.

Results

The clinical results obtained and the study of the evolution of biological tests of the HF-treated patients are listed in Tables 1-3 (appearing hereinbelow). During the first 10 days of HF treatment some subjective symptoms as asthenia, headache, insomnia or drowsiness, itching, lack of appetite, bitter taste in the morning, post-meal liver pain and muscular weakness, all of these progressively decreased during the ensuing two months of the treatment. The oedema and ascites in cirrhotic patients, where the usual diuretic treatment had failed, could now be influenced by association with HF; the diuretic dosage was reduced—it was administered only twice a week—and a proper diet was instituted. The splenomegaly and hepatomegaly diminished at the end of the first month of the treatment. The vascular stars and the hemorrhagic syndrome disappeared in the first two weeks after the beginning of the HF treatment. In two patients out of three, who reacted well to the HF therapy, an increase in body weight was noted; the oedema disappeared completely, leading to a suspension of the treatment for the diuretics and the patients were continued only on the diet.

The biological test evolution progressed parallel with the clinical improvement. The serum proteins increased 30 days after the treatment, in parallel with the increase of the protrombine synthesis. The BSP clearance improved in the majority of the patients and especially in patients with chronic hepatitis.

The hepatocytolysis and mesenchymal inflammation syndrome improved progressively, significant differences being obtained 60 days after the treatment.

The local and general HF tolerance was very good. No side effects were noticed.

Discussion

The majority of the patients experimented on were about 50 years old and, suffering from chronic aggressive hepatitis or decompensated liver cirrhosis, had been unable to develop any spontaneous improvement in their clinical status and in liver laboratory tests. Before the clinical HF trial, all the patients had used various conventional liver-protecting drugs, e.g. Purinor, Essentiale, Aspatofort and no improvement was noted either clinically or in the laboratory tests.

Patients having liver cirrhosis at the beginning of the experiment showed the oedema-ascitic syndrome and were refractory to the diuretics therapy. In these patients the HF therapy determined an improvement in their clinical status and laboratory tests, with exclusion of the influence of subjective factors related to the psychological effect of therapy with a new drug.

The therapeutic effects obtained in the HF experiment agreed with the results obtained by other teams working with chronic hepatitis and liver cirrhosis; the favorable effects can be accounted for by the active substances in the Hepatoprotector Factor at the level of the hepatocyte structure.

Conclusions

The HF clinical experiment in a group of 14 patients, 10 females and 4 males, 7 of them with chronic aggressive hepatitis and 7 with decompensated liver cirrhosis, demonstrated that:

the therapy with HF determined the improvement of clinical subjective and objective symptoms in 12 patients (7 with chronic hepatitis and 5 with liver cirrhosis), in 13 patients a favorable evolution of the laboratory tests was noticed, the results obtained in the experiment with HF led to the conclusion that HF is an efficacious drug for therapeutic use by patients with chronic aggressive hepatitis and liver cirrhosis.

TABLE 1

| | Mean values of laboratory tests before and after 60 days of HF treatment | | | |
|---|---|---|---|---|
| | Chronic hepatitis - 7 patients | | Liver cirrhosis - 7 patients | |
| Tests | initial value | final value | initial value | final value |
| Serines | 33.93 | 36.05 | 25.34 | 29.63 |
| Gammaglobuline | 30.02 | 27.90 | 31.98 | 28.76 |
| SGPT | 56.40 | 39.20 | 31.00 | 29.85 |
| Time Quick | 83.10% | 86.5% | 73.50% | 78.70% |
| Bilirubine (T) | 8.7 | 7.8 | 15.9 | 12.2 |
| r. Gross | 0.90 | 1.14 | 0.48 | 0.63 |
| r. Thymol | 13.0 | 10.0 | 16.0 | 13.0 |
| Colesterol | 1.60 | 1.80 | 1.46 | 1.51 |
| BSP | 11.0 | 10.0 | 14.0 | 13.0 |

TABLE 2

| | HF treatment influence of the clinical evolution of the patients | | |
|---|---|---|---|
| | | Clinical evolution | |
| Diagnosis | No. patients | Improved | Non-influenced |
| Chronic agressive hepatitis | 7 | 7 | — |
| Liver cirrhosis | 7 | 5 | 2 |

TABLE 3

The clinical symptoms and laboratory tests evolution under HF treatment in patients (H.C.A. = Chronic agressive hepatitis; CH = liver cirrhosis; F = invourable evolution; N = non-influence; i = initial value; f = final value)

| Nr. crt. | Patient Diagn. | Sex Age | Clin. evol. | Serine i | Serine f | Gammaglobuline i | Gammaglobuline f | T.G.P. i | T.G.P. f | T.Quick i | T.Quick f | Bilirub. i | Bilirub. f | Gross i | Gross f | Thymol i | Thymol f | Colesterol i | Colesterol f | B.S.P. i | B.S.P. f |
|---|---|---|---|---|---|---|---|---|---|---|---|---|---|---|---|---|---|---|---|---|---|
| 1 | P.A. H.C.A. | F 24 | F | 30.75 | 31.25 | 24.42 | 19.60 | 70 | 60 | 66 | 80 | 10 | 9 | 0.90 | 0 | 8 | 8 | 2.40 | 2.42 | 17 | 16 |
| 2 | G.M. H.C.A. | F 53 | F | 22.73 | 28.33 | 36.40 | 33.25 | 40 | 35 | 80 | 80 | 11 | 11 | 0.60 | 1.10 | 14 | 10 | 2.00 | 2.08 | 8 | 8 |

TABLE 3-continued

The clinical symptoms and laboratory tests evolution under HF treatment in patients (H.C.A. = Chronic agressive hepatitis; CH = liver cirrhosis; F = invourable evolution; N = non-influence; i = initial value; f = final value)

| Nr. crt. | Patient Diagn. | Sex Age | Clin. evol. | Serine i | Serine f | Gammaglobuline i | Gammaglobuline f | T.G.P. i | T.G.P. f | T.Quick i | T.Quick f | Bilirub. i | Bilirub. f | Gross i | Gross f | Thymol i | Thymol f | Colesterol i | Colesterol f | B.S.P. i | B.S.P. f |
|---|---|---|---|---|---|---|---|---|---|---|---|---|---|---|---|---|---|---|---|---|---|
| 3 | S.V. C.H. | M 64 | N | 24.03 | 25.08 | 24.00 | 26.37 | 32 | 20 | 73 | 80 | 14 | 11 | 0.30 | 0.40 | 14 | 11 | 1.56 | 1.58 | 14 | 13 |
| 4 | H.V. C.H. | M 56 | F | 24.75 | 27.15 | 30.30 | 28.30 | 32 | 20 | 66 | 78 | 13 | 12 | 0.10 | 0.20 | 15 | 13 | 1.60 | 1.50 | 17 | 16 |
| 5 | Z.M. C.H. | F 58 | N | 23.80 | 22.00 | 36.36 | 36.81 | 35 | 30 | 65 | 65 | 27 | 16 | 0.20 | 0.30 | 16 | 15 | 1.34 | 1.26 | 17 | 17 |
| 6 | M.E. C.H. | F 57 | F | 19.68 | 20.50 | 29.76 | 28.00 | 28 | 25 | 68 | 78 | 17 | 14 | 0.40 | 0.50 | 18 | 16 | 1.10 | 1.20 | 18 | 16 |
| 7 | S.E. H.C.A. | F 38 | F | 47.84 | 42.36 | 23.00 | 21.15 | 15 | 15 | 91 | 100 | 9 | 9 | 1.20 | 1.30 | 7 | 5 | 1.68 | 1.80 | 10 | 8 |
| 8 | L.E. C.H. | M 56 | F | 28.88 | 40.11 | 37.08 | 26.46 | 40 | 32 | 80 | 85 | 16 | 12 | 0.70 | 0.90 | 10 | 8 | 1.70 | 1.70 | 12 | 11 |
| 9 | G.E. C.H. | F 70 | F | 22.92 | 37.95 | 34.00 | 28.91 | 32 | 62 | 78 | 85 | 11 | 10 | 0.75 | 1.10 | 16 | 9 | 1.40 | 1.60 | 14 | 12 |
| 10 | D.C. H.C.A. | F 43 | F | 30.25 | 34.90 | 29.60 | 27.07 | 42 | 35 | 80 | 95 | 11 | 10 | 1.30 | 1.40 | 9 | 9 | 2.10 | 2.55 | 13 | 12 |
| 11 | S.M. C.H. | F 72 | F | 33.32 | 35.20 | 30.36 | 31.50 | 18 | 20 | 85 | 87 | 12 | 11 | 0.70 | 0.90 | 9 | 8 | 1.68 | 1.76 | 12 | 11 |
| 12 | N.S. H.C.A. | F 40 | F | 37.04 | 43.00 | 25.48 | 24.31 | 12 | 10 | 80 | 65 | 3 | 4 | 0.80 | 0.90 | 8 | 10 | 2.00 | 1.80 | 0 | 8 |
| 13 | C.A. H.C.A. | M 53 | F | 35.40 | 39.40 | 39.00 | 31.60 | 152 | 52 | 76 | 80 | 4 | 4 | 0.90 | 1.00 | 24 | 14 | 1.60 | 2.00 | 12 | 11 |
| 14 | E.E. H.C.A. | F 19 | F | 33.50 | 41.00 | 37.00 | 33.50 | 88 | 45 | 100 | 100 | 10 | 8 | 1.10 | 1.40 | 19 | 15 | 2.00 | 2.00 | 10 | 0 |

I claim:

1. A method of treating liver cirrhosis or viral hepatitis which comprises administering to the patient a pharmaceutically effective amount of the Hepatoprotector Factor (HF) obtained from cattle liver by the following steps:
   (a) mincing the cattle liver;
   (b) extracting the minced cattle liver with acetone using about 3 kg of 70% acetone solution per kg of liver to form a liver extract in acetone;
   (c) pressing the minced cattle liver to separate the liver extract in acetone form the minced cattle liver;
   (d) filtering the miced cattle liver in acetone to remove impurities;
   (e) evaporating the acetone from the liver extract; then
   (f) extracting fat from the liver extract with a hydrophobic organic solvent;
   (g) subjecting the liver extract to gel filtration on an SP Sephadex C-25 column and eluting the gel with distilled water to recover a fraction having an absorption peak corresponding to the absorption peak I of FIG. 1 of the drawing where said fraction contains the Hepatoprotector Factor (HF);
   (h) lyophilizing the fraction separated out during step (g); and
   (i) dissolving the lyophilized product obtained in step (h) in distilled water and chemically ascertaining the quality of the Hepatoprotector Factor (HF) by at least one of the following methods:
      (1) elementary analysis;
      (2) amino acid analysis; or
      (3) high-voltage electrophoresis, and
   comparing the results against a known standard.

2. The method defined in claim 1 the product tested during step (i) is lyophilized.

* * * * *